US008741028B2

(12) United States Patent
Muraoka et al.

(10) Patent No.: US 8,741,028 B2
(45) Date of Patent: Jun. 3, 2014

(54) CARBON DIOXIDE SEPARATING AND RECOVERING SYSTEM AND METHOD OF CONTROLLING THE SAME

(75) Inventors: Daigo Muraoka, Tokyo (JP); Koshito Fujita, Yokohama (JP); Takashi Ogawa, Yokohama (JP); Hideo Kitamura, Tokyo (JP); Satoshi Saito, Yamato (JP); Masatoshi Hodotsuka, Saitama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 102 days.

(21) Appl. No.: 13/343,221

(22) Filed: Jan. 4, 2012

(65) Prior Publication Data
US 2012/0167760 A1 Jul. 5, 2012

(30) Foreign Application Priority Data

Jan. 5, 2011 (JP) ................................. 2011-000727
Dec. 22, 2011 (JP) ................................. 2011-281295

(51) Int. Cl.
*B01D 53/14* (2006.01)
(52) U.S. Cl.
USPC ............. 95/8; 96/244; 96/251; 95/14; 95/236
(58) Field of Classification Search
None
See application file for complete search history.

(56) References Cited

U.S. PATENT DOCUMENTS

| 5,757,660 A | 5/1998 | Musow |
| 6,350,426 B1 | 2/2002 | Sota et al. |
| 2003/0022386 A1 | 1/2003 | Swallow et al. |
| 2003/0045756 A1 | 3/2003 | Mimura et al. |
| 2009/0211447 A1* | 8/2009 | Lichtfers et al. ................ 95/201 |
| 2012/0067219 A1 | 3/2012 | Ogawa et al. |

FOREIGN PATENT DOCUMENTS

| EP | 2 418 470 A1 | 2/2012 |
| JP | 2002-71647 A | 3/2002 |
| JP | 2004-323339 A | 11/2004 |
| JP | 2006-078334 A | 3/2006 |
| JP | 2006078334 A * | 3/2006 |
| WO | WO 2010/116892 A1 | 10/2010 |
| WO | WO 2010116892 A1 * | 10/2010 |

OTHER PUBLICATIONS

English translation of JP2006078334.*
English translation of WO2010116892.*

(Continued)

*Primary Examiner* — Duane Smith
*Assistant Examiner* — Phillip Shao
(74) *Attorney, Agent, or Firm* — Holtz Holtz Goodman & Chick PC

(57) ABSTRACT

In one embodiment, a carbon dioxide separating and recovering system includes an absorption tower to cause carbon dioxide to be absorbed in an absorbing solution, a regeneration tower to release the carbon dioxide from the absorbing solution, and at least one measuring apparatus to measure an ultrasound propagation speed in the absorbing solution. Each of the at least one measuring apparatus calculates a dissolved carbon dioxide concentration in the absorbing solution, based on a temperature measured by a temperature measuring unit, the ultrasound propagation speed measured by an ultrasound propagation speed measuring unit, and a correlation expression which shows a relationship between the dissolved carbon dioxide concentration and the ultrasound propagation speed in the absorbing solution, and is changed according to the temperature of the absorbing solution. The carbon dioxide separating and recovering system controls the system, based on the dissolved carbon dioxide concentration calculated by the measuring apparatus.

5 Claims, 9 Drawing Sheets

(56) References Cited

OTHER PUBLICATIONS

Canadian Office Action dated Apr. 3, 2013 (in English) issued in counterpart Canadian Application No. 2,763,176.
Partial European Search Report (PESR) dated Apr. 12, 2012, in counterpart European Application No. 11196086.0.
Extended European Search Report (EESR) dated Jul. 12, 2012 (in English) in counterpart European Application No. 11196086.0.
Australian Office Action dated Feb. 21, 2013 (in English) issued in counterpart Australian Application No. 2012200039.
Australian Office Action dated Jan. 2, 2013 in counterpart Australian Application No. 2012200039.
Chinese Office Action dated Jan. 21, 2014 (and English translation thereof) in counterpart Chinese Application No. 201210001605.3.

* cited by examiner

CARBON DIOXIDE SEPARATING AND RECOVERING SYSTEM AND METHOD OF CONTROLLING THE SAME

CROSS REFERENCE TO RELATED APPLICATIONS

This application is based upon and claims the benefit of priority from the prior Japanese Patent Applications No. 2011-000727, filed on Jan. 5, 2011 and No. 2011-281295, filed on Dec. 22, 2011, the entire contents of which are incorporated herein by reference.

FIELD

Embodiments described herein relate to a carbon dioxide separating and recovering system and a method of controlling the same, for example, for separating and recovering carbon dioxide in a combustion exhaust gas.

BACKGROUND

In recent years, the importance of the problem of global warming has become increased due to the greenhouse effect of carbon dioxide ($CO_2$) that is a product of combustion of fossil fuel. In the Kyoto Protocol to the United Nations Framework Convention on Climate Change, Japan's goal in reducing the greenroom effect gas emissions is to attain an 8% reduction from the amount of emissions in 1990.

With such a background, studies are energetically made regarding a method of separating and recovering carbon dioxide in a combustion exhaust gas by bringing the combustion exhaust gas and an amine-based absorbing solution into contact with each other, and a method of storing recovered carbon dioxide without releasing carbon dioxide into atmospheric air.

An example of the method of separating and recovering carbon dioxide by using such an absorbing solution includes a step of causing the carbon dioxide in the combustion exhaust gas to be absorbed in the absorbing solution by bringing the combustion exhaust gas and the absorbing solution into contact with each other in an absorption tower, and a step of purging the carbon dioxide from the absorbing solution containing the absorbed carbon dioxide by heating the absorbing solution in a regeneration tower (refer to JP-A 2004-323339 (KOKAI)). The absorbing solution purged of the carbon dioxide is again supplied to the absorption tower to be reused.

JP-A 2002-71647 (KOKAI) discloses an example of a method of measuring a concentration of dissolved carbon dioxide by using ultrasound.

DETAILED DESCRIPTION

Figure 1:
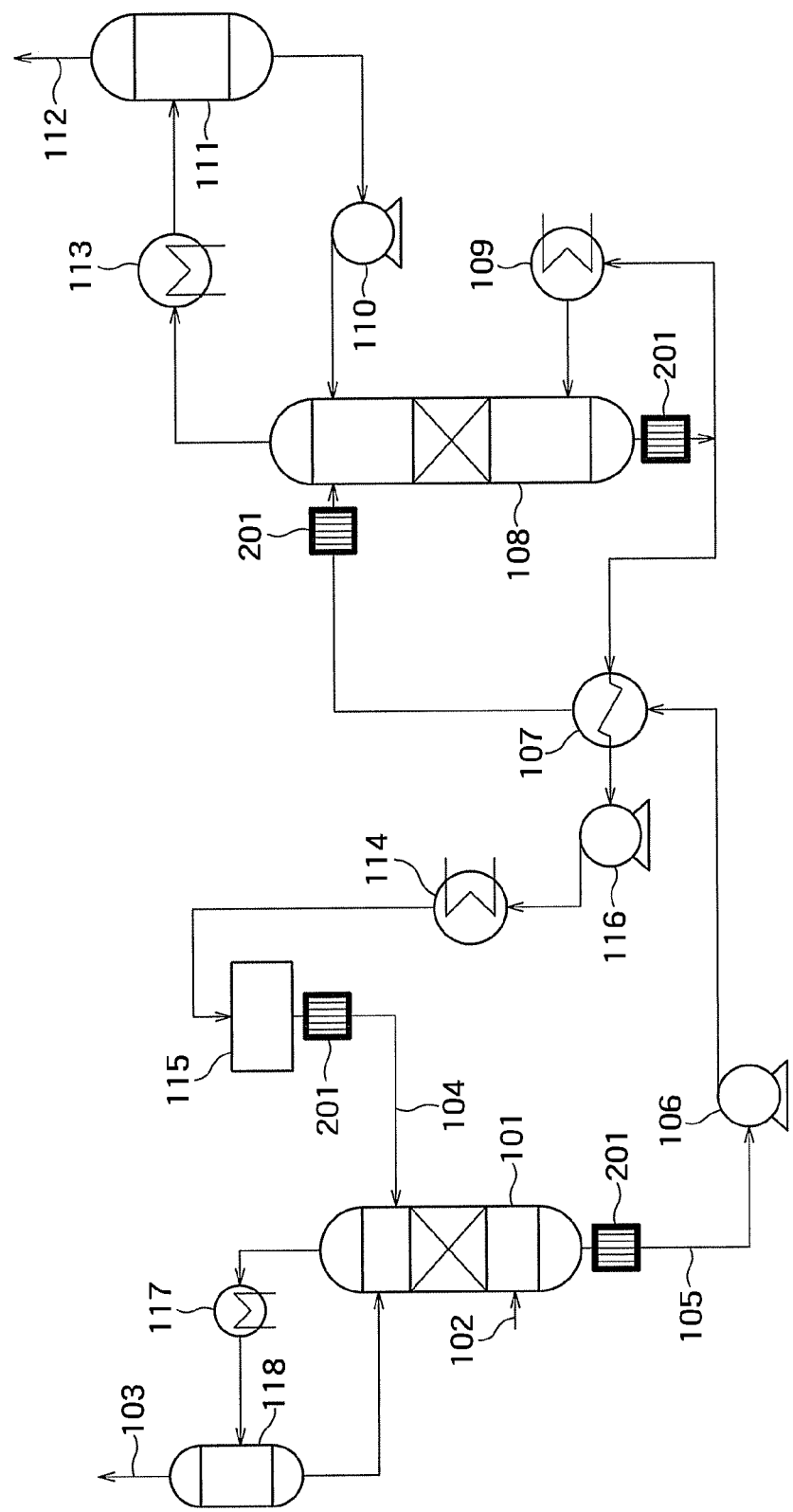
FIG. 1 is a diagram showing the construction of a carbon dioxide separating and recovering system in a first embodiment.

Embodiments will now be explained with reference to the accompanying drawings.

As described above, the process in a carbon dioxide separating and recovering system includes two steps, i.e., a step of causing the carbon dioxide to be absorbed in the absorbing solution in the absorption tower, and a step of purging the absorbed carbon dioxide from the absorbing solution in the regeneration tower.

To operate this system with stability, it is important to maintain a state in which the concentration of dissolved carbon dioxide which is absorbed in the absorbing solution in the absorption tower coincides with the concentration of dissolved carbon dioxide which is released from the absorbing solution in the regeneration tower at all times. In other words, it is required to perform an operation so that the difference between the dissolved carbon dioxide concentrations in a rich solution at an outlet of the absorption tower and a lean solution at an inlet of the absorption tower is set equal to the difference between the dissolved carbon dioxide concentrations in the rich solution at an inlet of the regeneration tower and the lean solution at an outlet of the regeneration tower.

For example, when the dissolved carbon dioxide concentration in the lean solution at the outlet of the regeneration tower is higher than that in the lean solution at the inlet of the absorption tower, a predetermined amount of carbon dioxide cannot be absorbed in the absorption tower unless the amount of loading of the lean solution at the outlet of the regeneration tower is reduced by increasing thermal energy inputted to a regeneration tower reboiler. Conversely, when the dissolved carbon dioxide concentration in the lean solution at the outlet of the regeneration tower is lower than that in the lean solution at the inlet of the absorption tower, thermal energy more than required is inputted to the regeneration tower reboiler.

In this way, to adjust thermal energy inputted to the regeneration tower reboiler while monitoring the dissolved carbon dioxide concentration in the absorbing solution is required for stable economical operation of the system. However, a gas chromatograph (thermal conductivity detector (TCD)) presently used as a technique to measure the dissolved carbon dioxide concentration, requires certain technical work and measuring time (required time: about 15 minutes). Therefore, if this technique is used, the dissolved carbon dioxide concentration cannot be monitored on time, so that the carbon dioxide separating and recovering system cannot be operated with stability.

On the other hand, it is confirmed that the operation of the carbon dioxide separating and recovering system causes the occurrence of decomposition of absorbing solution components and the production of impurity product ions. Furthermore, it is known that the carbon dioxide absorbing performance of the absorbing solution is reduced due to such phenomena. Therefore, to stably-operate the carbon dioxide separating and recovering system, it is required to add absorbing solution components and remove impurity product ions as appropriate.

According to a conventional post-combustion carbon dioxide recovering method, it is difficult to measure the dissolved carbon dioxide concentration in the absorbing solution on time, because the composition and physical properties of the used absorbing solution always change depending on operating conditions. Therefore, the measurement of the dissolved carbon dioxide concentration requires time and operations for fixing the measuring conditions, taking samples to be measured, performing pre-processing and the like. Also, no method has been established to enable on-time grasping of the concentration of the dissolved carbon dioxide that is chemically adsorbed to amine in the absorbing solution.

An embodiment described herein is a carbon dioxide separating and recovering system including an absorption tower configured to cause carbon dioxide to be absorbed in an absorbing solution, and exhaust a rich solution as the absorbing solution in which the carbon dioxide is absorbed, and a regeneration tower configured to release the carbon dioxide from the rich solution, and exhaust a lean solution as the absorbing solution having a dissolved carbon dioxide concentration lower than a dissolved carbon dioxide concentration in the rich solution. The system further includes at least one measuring apparatus configured to measure an ultrasound propagation speed in the absorbing solution flowing in the system. Each of the at least one measuring apparatus includes a temperature measuring unit configured to measure a temperature of the absorbing solution, an ultrasound generator configured to generate ultrasound in the absorbing solution, and an ultrasound propagation speed measuring unit configured to measure the ultrasound propagation speed by using the ultrasound. Each of the at least one measuring apparatus further includes a dissolved carbon dioxide concentration calculator configured to calculate a dissolved carbon dioxide concentration in the absorbing solution, based on the temperature measured by the temperature measuring unit, the ultrasound propagation speed measured by the ultrasound propagation speed measuring unit, and a correlation expression which shows a relationship between the dissolved carbon dioxide concentration and the ultrasound propagation speed in the absorbing solution, and is changed according to the temperature of the absorbing solution. The carbon dioxide separating and recovering system is configured to control the system, based on the dissolved carbon dioxide concentration calculated by the measuring apparatus.

Another embodiment described herein is a carbon dioxide separating and recovering system including an absorption tower configured to cause carbon dioxide to be absorbed in an absorbing solution, and exhaust a rich solution as the absorbing solution in which the carbon dioxide is absorbed, and a regeneration tower configured to release the carbon dioxide from the rich solution, and exhaust a lean solution as the absorbing solution having a dissolved carbon dioxide concentration lower than a dissolved carbon dioxide concentration in the rich solution. The system further includes at least one measuring apparatus configured to measure electric conductivity of the absorbing solution flowing in the system. Each of the at least one measuring apparatus includes a temperature measuring unit configured to measure a temperature of the absorbing solution, and an electric conductivity measuring unit configured to measure the electric conductivity of the absorbing solution. Each of the at least one measuring apparatus further includes an ion concentration calculator configured to calculate an ion concentration in the absorbing solution, based on the temperature measured by the temperature measuring unit, the electric conductivity measured by the electric conductivity measuring unit, and a correlation expression which shows a relationship between the ion concentration and the electric conductivity in the absorbing solution, and is changed according to the temperature of the absorbing solution. The carbon dioxide separating and recovering system is configured to control the system, based on the ion concentration calculated by the measuring apparatus.

First Embodiment

FIG. 1 is a diagram showing the construction of a carbon dioxide separating and recovering system in a first embodiment.

In the system shown in FIG. 1, a $CO_2$ containing gas 102, which is combustion exhaust gas, is supplied into an absorption tower. The absorption tower is constructed so as to cause $CO_2$ to be absorbed in an absorbing solution by bringing the $CO_2$ containing gas 102 and the absorbing solution into contact with each other. As the absorbing solution, in the present embodiment, an amine-based absorbing solution, for example, is used.

In a lower portion of the absorption tower 101, the absorbing solution that has absorbed $CO_2$ and contains dissolved carbon dioxide at a high concentration (rich solution 105) is collected. The rich solution 105 collected in the lower portion of the absorption tower 101 is exhausted through an outlet provided in the lower portion of the absorption tower 101 and transferred from the outlet of the absorption tower 101 to an inlet provided in an upper portion of a regeneration tower 108 by a rich solution transferring pump 106 to be supplied to the interior of the regeneration tower 108 through the inlet of the same.

The rich solution 105 supplied into the regeneration tower 108 falls from the upper portion of the regeneration tower 108. With this process, an absorbing solution called lean solution 104 is collected in a lower portion of the regeneration tower 108. The lean solution 104 collected in the lower portion of the regeneration tower 108 is exhausted through an outlet provided in the lower portion of the regeneration tower 108, heated by a regeneration tower reboiler 109 and thereafter supplied into the regeneration tower 108 again. In this way, the lean solution 104 is heated while being circulated between the regeneration tower 108 and the regeneration tower reboiler 109. $CO_2$ in the lean solution 104 is thereby released as $CO_2$ gas. $CO_2$ is released from the lean solution 104 in this way, so that the dissolved carbon dioxide concentration in the lean solution 104 is lower than that in the rich solution 105.

$CO_2$ gas released from the lean solution 104 is exhausted from the upper portion of the regeneration tower 108 together with water vapor simultaneously evaporated from the lean solution 104. A gas mixture of the exhausted $CO_2$ gas and water vapor is cooled by a regeneration tower reflux cooler 113. Water vapor is thereby condensed to become water again. The mixture fluid consisting of the condensed water and $CO_2$ gas flows into a $CO_2$ separator 111. The $CO_2$ separator 111 separates the $CO_2$ gas from the condensed water and exhausts only the $CO_2$ gas from a recovered $CO_2$ exhaust line 112. On the other hand, the condensed water is taken out from an outlet in a lower portion of the $CO_2$ separator 111 and returned to the regeneration tower 108 by a reflux solution pump 110.

Also, after the lean solution 104 collected in the lower portion of the regeneration tower 108 is exhausted through the outlet in the lower portion of the regeneration tower 108, part of the exhausted lean solution 104 is transferred from the outlet of the regeneration tower 108 to an inlet provided in an upper portion of the absorption tower 101 by a lean solution transferring pump 116 to be supplied to the interior of the absorption tower 101 through the inlet of the same. This lean solution 104 is thereafter used as the absorbing solution for absorbing $CO_2$ in the absorption tower 101.

In FIG. 1, a regenerated heat exchanger 107, a lean solution cooler 114 and a lean solution buffer tank 115 are also shown.

The regenerated heat exchanger 107 is disposed at a point at which a channel extending from the outlet of the absorption tower 101 to the inlet of the regeneration tower 108 and a channel extending from the outlet of the regeneration tower 108 to the inlet of the absorption tower intersect each other. The regenerated heat exchanger 107 is a heat exchanger that heats the rich solution 105 about to flow into the regeneration tower 108 by heat remaining in the lean solution 104 heated by the regeneration tower reboiler 109 and exhausted.

The lean solution cooler 114 and the lean solution buffer tank 115 are disposed on a channel extending from the outlet of the regeneration tower 108 to the inlet of the absorption tower 101. The lean solution cooler 114 is a cooler for cooling the lean solution 104 after passage through the regenerated heat exchanger 107. The lean solution buffer tank 115 is a tank for storing the lean solution 104 passed through the lean solution cooler 114 before the lean solution 104 is caused to flow into the absorption tower 101.

Further, an absorption tower reflux cooler 117 and a vapor-liquid disengager 118 are shown in FIG. 1.

In the absorption tower 101, after the combustion exhaust gas ($CO_2$ containing gas 102) provided as a gas from which carbon dioxide is to be separated and recovered is brought into contact with the absorbing solution to perform absorption of $CO_2$, the combustion exhaust gas is exhausted from the upper portion of the absorption tower 101 together with water vapor evaporated from the absorbing solution. A gas as a mixture of the exhausted combustion exhaust gas and water vapor is cooled by the absorption tower reflux cooler 117. Water vapor is thereby condensed to become water again. The mixture fluid consisting of the condensed water and the combustion exhaust gas flows into the vapor-liquid disengager 118. The vapor-liquid disengager 118 separates the combustion exhaust gas (gas) and the condensed water (liquid) from each other and exhausts the separated combustion exhaust gas as $CO_2$-removed exhaust gas 103. On the other hand, the condensed water is taken out from the outlet in the lower portion of the vapor-liquid disengager 118 to be returned to the absorption tower 101.

System control in the present embodiment will be described below in detail. In the present embodiment, the dissolved $CO_2$ concentration (dissolved carbon dioxide concentration) in the absorbing solution is calculated on time and system control is performed based on the calculated dissolved $CO_2$ concentration.

In the system shown in FIG. 1, when the mass balance between the dissolved $CO_2$ concentration in the lean solution 104 flowing through the inlet of the absorption tower 101 and the dissolved $CO_2$ concentration in the lean solution 104 flowing through the outlet of the regeneration tower 108 is lost, it is necessary to change the amount of heat inputted to the regeneration tower reboiler 109. However, unless the system can be monitored on time, grasping of the mass balance of the amount of heat inputted to the regeneration tower reboiler 109 is retarded and there is, therefore, a possibility of occurrence of a loss of energy or a reduction in recovery rate.

In the system shown in FIG. 1, in the present embodiment, therefore, one or more ultrasound propagation speed measuring apparatuses 201 that measure the speed of propagation of ultrasound in the absorbing solution flowing in the system is disposed.

In the present embodiment, the measuring apparatuses 201 are disposed in the vicinities of the inlets and the outlets of the absorption tower 101 and the regeneration tower 108. In FIG. 1, the four measuring apparatuses 201 disposed at such positions are shown. In the present embodiment, with these measuring apparatuses 201, the speeds of propagation of ultrasound in the lean solution 104 flowing in the vicinity of the inlet of the absorption tower 101, the rich solution 105 flowing in the vicinity of the outlet of the absorption tower 101, the rich solution 105 flowing in the vicinity of the inlet of the regeneration tower 108, and the lean solution 104 flowing in the vicinity of the outlet of the regeneration tower 108 are measured. The measuring apparatuses 201 are an example of the first to fourth measuring apparatuses in the disclosure. In the present embodiment, each of the measuring apparatuses 201 is set in the channel in which the absorbing solution flows (absorbing solution piping).

Figure 2:
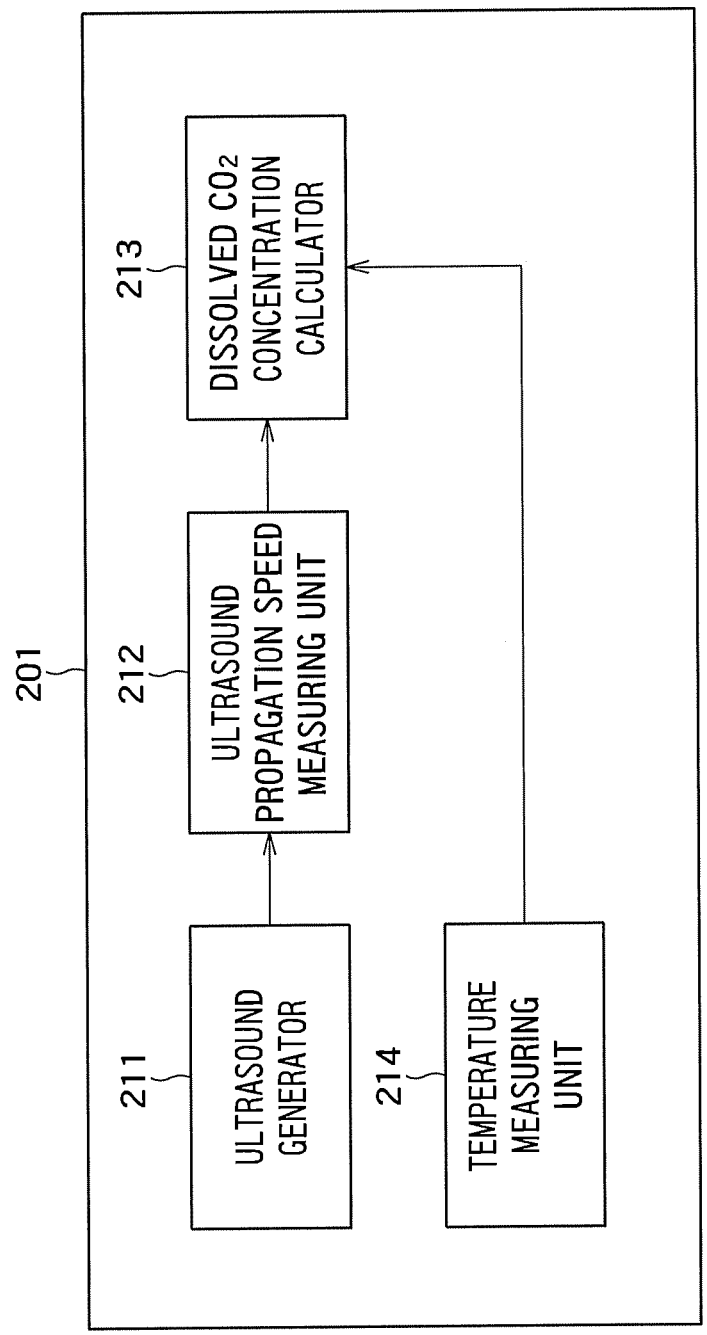
FIG. 2 is a block diagram showing a configuration of an ultrasound propagation speed measuring apparatus in FIG. 1.

FIG. 2 is a block diagram showing a configuration of the ultrasound propagation speed measuring apparatuses 201 in FIG. 1. Each of the ultrasound propagation speed measuring apparatuses 201 shown in FIG. 1 is assumed to have the configuration shown in FIG. 2.

The ultrasound propagation speed measuring apparatus 201 has, as shown in FIG. 2, an ultrasound generator 211, an ultrasound propagation speed measuring unit 212, a dissolved $CO_2$ concentration calculator 213 and a temperature measuring unit 214.

The ultrasound generator 211 is a device that generates ultrasound in the absorbing solution flowing in the measuring apparatus 201. The ultrasound generator 211 is constituted by an ultrasonic vibrator, for example.

The ultrasound propagation speed measuring unit 212 is a device that measures the speed of propagation of ultrasound in the absorbing solution by using ultrasound from the ultrasound generator 211. The ultrasound propagation speed measuring unit 212 in the present embodiment measures the ultrasound propagation speed (i.e., sound velocity) by measuring the time period before return of a reflected wave of ultrasound from a reflecting plate positioned at a certain distance from the ultrasound propagation speed measuring unit 212.

Figure 8:
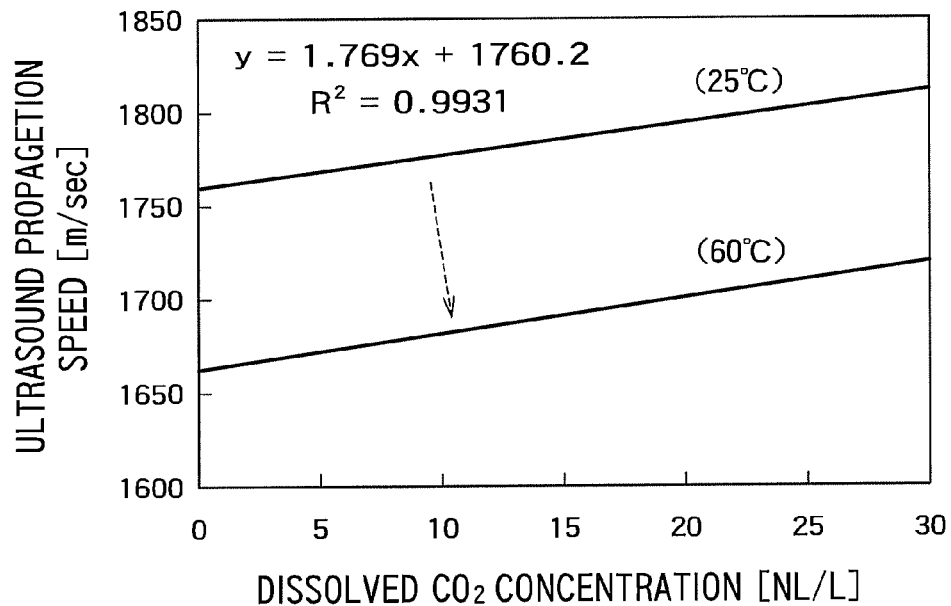
FIG. 8 is a graph showing the relationship between the dissolved $CO_2$ concentration and the ultrasound propagation speed.

The ultrasound propagation speed in the absorbing solution is a parameter usable for calculation of the dissolved $CO_2$ concentration in the absorbing solution, as described below with reference to FIG. 8. FIG. 8 is a graph showing the relationship between the dissolved $CO_2$ concentration and the ultrasound propagation speed in the absorbing solution. As shown in FIG. 8, the ultrasound propagation speed in the absorbing solution changes according to the dissolved $CO_2$ concentration in the absorbing solution. Therefore, the dissolved $CO_2$ concentration in the absorbing solution can be calculated from the ultrasound propagation speed in the absorbing solution.

Figure 9:
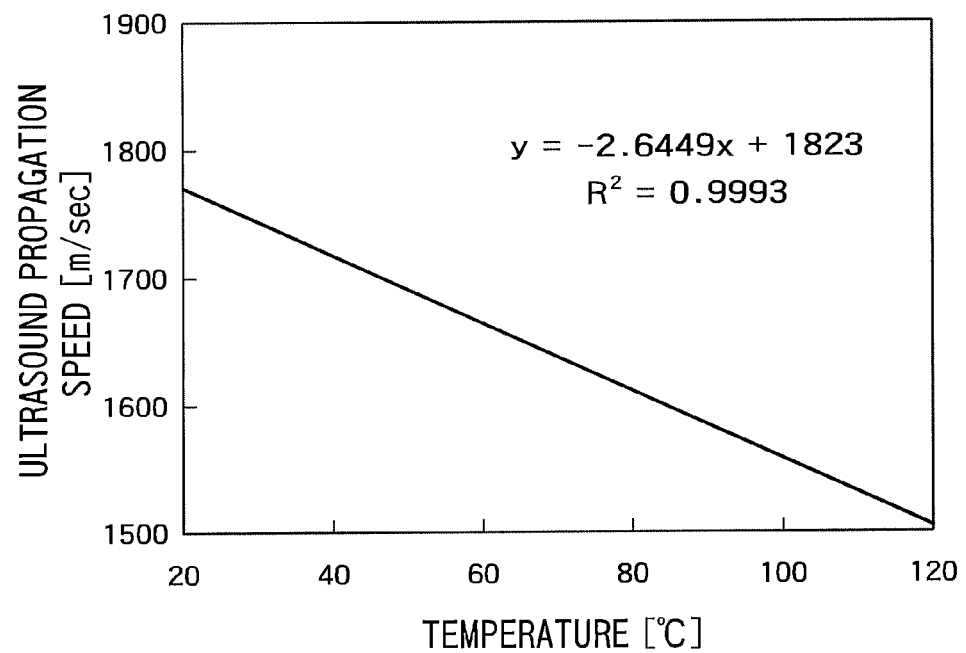
FIG. 9 is a graph showing the relationship between the temperature and the ultrasound propagation speed.

However, the ultrasound propagation speed in the absorbing solution also changes depending on the temperature of the absorbing solution, as shown in FIG. 9. FIG. 9 is a graph showing the relationship between the temperature and the ultrasound propagation speed in the absorbing solution. As shown in FIG. 9, the ultrasound propagation speed has a temperature dependence. Therefore, a correlation expression shown in FIG. 8 is changed according to the temperature of the absorbing solution. FIG. 8 shows the correlation expression at 25° C. and at 60° C., i.e., a state in which the correlation expression is changed according to the temperature.

As described above, the dissolved $CO_2$ concentration in the absorbing solution can be calculated from the ultrasound propagation speed in the absorbing solution. In the present embodiment, therefore, a correlation expression showing the relationship between the ultrasound propagation speed and the dissolved $CO_2$ concentration in the absorbing solution is obtained in advance and saved in the measuring apparatus 201. In the present embodiment, a straight line expressed by this correlation expression, such as shown in FIG. 8, is used as a measuring line for measuring the dissolved $CO_2$ concentration. In this way, the measuring apparatus 201 can calculate the dissolved $CO_2$ concentration from the ultrasound propagation speed.

However, the above-described correlation expression has a temperature dependence. In the present embodiment, therefore, the above-described correlation expressions at various temperatures are saved in the measuring apparatus 201. Alternatively, a fixed expression including temperature as a parameter is formed from the above-described correlation expression and saved in the measuring apparatus 201, thus enabling calculation of the dissolved $CO_2$ concentration taking temperature compensation into consideration.

The measuring apparatus 201 in the present embodiment calculates the dissolved $CO_2$ concentration in the absorbing solution based on the temperature of the absorbing solution, the ultrasound propagation speed in the absorbing solution and the above-described correlation expression. The dissolved $CO_2$ concentration calculator 213 and the temperature measuring unit 214 (see FIG. 2), which are blocks relating to this processing, will be described below in detail.

The temperature measuring unit 214 is a thermometer that measures the temperature of the absorbing solution. The temperature measuring unit 214 in the present embodiment is disposed in the vicinity or a place through which the above-described ultrasound propagates.

The dissolved $CO_2$ concentration calculator 213 is a block for calculating the dissolved $CO_2$ concentration in the absorbing solution on the basis of the temperature measured by the temperature measuring unit 214, the ultrasound propagation speed measured by the ultrasound propagation speed measuring unit 212, and the above-described correlation expression. For example, the dissolved $CO_2$ concentration calculator 213 is constituted by a storage unit capable of storing the above-described correlation expression and a calculator that performs processing for calculating the dissolved $CO_2$ concentration.

In the present embodiment, as described above, a method of calculating the dissolved $CO_2$ concentration in the absorbing solution from the ultrasound propagation speed in the absorbing solution is adopted. Unlike gas chromatography, this method has the advantage of enabling on-time grasping of the dissolved $CO_2$ concentration. In the present embodiment, therefore, the system can be stably and economically operated by adjusting the amount of heat inputted to the regeneration tower reboiler 109 while monitoring the dissolved $CO_2$ concentration in the absorbing solution on time, as described below.

Also, the dissolved $CO_2$ concentration as the sum of the concentration of dissolved $CO_2$ chemically adsorbed to an amine in the absorbing solution and the concentration of dissolved $CO_2$ physically adsorbed to water contributes to a change in ultrasound propagation speed in the absorbing solution. In the present embodiment, therefore, the dissolved $CO_2$ concentration obtained by combining these two kinds of solute concentration can be grasped.

System control in the present embodiment performed based on the dissolved $CO_2$ concentration calculated by the measuring apparatus 201 will be described below in detail.

In the system shown in FIG. 1, the dissolved $CO_2$ concentrations in the absorbing solutions flowing in the vicinities of the inlets and outlets of the absorption tower 101 and the regeneration tower 108 are calculated by the four measuring apparatuses 201, as described above. The dissolved $CO_2$ concentrations in the vicinities of the inlet of the absorption tower 101, the outlet of the absorption tower 101, the inlet of the regeneration tower 108 and the outlet of the regeneration tower 108 are represented by $X_1$, $X_2$, $Y_1$ and $Y_2$, respectively.

Further, in the system shown in FIG. 1, the difference $\Delta X (=X_2-X_1)$ between the dissolved $CO_2$ concentrations $X_1$ and $X_2$ in the vicinity of the inlet and the outlet of the absorption tower 101 and the difference $\Delta Y (=Y_1-Y_2)$ between the dissolved $CO_2$ concentrations $Y_1$ and $Y_2$ in the vicinity of the inlet and the outlet of the regeneration tower 108 are calculated by using the $CO_2$ concentrations $X_1$, $X_2$, $Y_1$ and $Y_2$. In the system shown in FIG. 1, control of the system is performed based on the difference $\Delta X$ in the absorption tower 101 and the difference $\Delta Y$ in the regeneration tower 108.

In the present embodiment, control based on the differences $\Delta X$ and $\Delta Y$ is performed, as described below.

For example, when the difference $\Delta Y$ in the regeneration tower 108 is larger than the difference $\Delta X$ in the absorption tower 101, a state where thermal energy more than required is being input to the regeneration tower reboiler 109 is recognized. Then, in the system shown in FIG. 1, the operation of the regeneration tower reboiler 109 is controlled so that the thermal energy input to the regeneration tower reboiler 109 is reduced.

Conversely, when the difference $\Delta Y$ in the regeneration tower 108 is smaller than the difference $\Delta X$ in the absorption tower 101, a state where the thermal energy input to the regeneration tower reboiler 109 is insufficient is recognized. Then, in the system shown in FIG. 1, the operation of the regeneration tower reboiler 109 is controlled so that the thermal energy input to the regeneration tower reboiler 109 is increased.

In the present embodiment, the dissolved $CO_2$ concentrations $X_1$, $X_2$, $Y_1$ and $Y_2$ can be grasped on time, as described above. According to the present embodiment, therefore, the system can be stably and economically operated by adjusting the amount of heat inputted to the regeneration tower reboiler 109 while monitoring on time the differences $\Delta X$ and $\Delta Y$ calculated from the dissolved $CO_2$ concentrations $X_1$, $X_2$, $Y_1$ and $Y_2$. That is, according to the present embodiment, the stability of the system can be improved and the cost for operation of the system can be reduced.

In the present embodiment, determination may be made as to whether the difference between $\Delta X$ and $\Delta Y$ exceeds an upper limit or a lower limit instead of comparison between the value of $\Delta X$ and the value of $\Delta Y$. In such a case, the thermal energy input to the regeneration tower reboiler 109 is reduced when $\Delta Y-\Delta X$ becomes equal to or larger than the upper limit, and the thermal energy input to the regeneration tower reboiler 109 is increased when $\Delta Y-\Delta X$ becomes equal to or smaller than the lower limit. The upper limit and the lower limit are set to ±5% (preferably ±1%). More specifically, the upper limit is set to $\Delta Y/\Delta X=1.05$ (preferably 1.01) and the lower limit is set to $\Delta Y/\Delta X=0.95$ (preferably 0.99).

In the above-described system control in the present embodiment, control of the flow rate of the $CO_2$ containing gas 102 supplied to the absorption tower 101, the circulation flow rate of the rich solution 105 flowed from the absorption tower 101 to the regeneration tower 108, the flow rate of the lean solution 104 flowing between the regeneration tower 108, the regeneration tower reboiler 109 and the absorption tower 101 or a condition for agitation in the lean solution buffer tank 115 may be performed instead of control of the amount of heat inputted to the regeneration tower reboiler 109. Two or more of these operating conditions may alternatively be controlled. Through control of these operating conditions, stable economical operation of the system can also be realized. It is important to set these operating conditions by considering mutual balance therebetween. It is, therefore, thought that it is desirable to control two or more of these operating conditions in the above-described system control in many cases.

In the present embodiment, the block for calculating the differences ΔX and ΔY and the block for performing the above-described system control may be disposed in arbitrary places in the system shown in FIG. 1. For example, in a case where only a condition for the operation of the regeneration tower reboiler 109 is to be controlled, a control unit provided on the regeneration tower reboiler 109 may perform calculation of the differences ΔX and ΔY and the above-described system control. In a case where two or more operating conditions are to be controlled, a calculator provided in a control room for the system shown in FIG. 1 or at a site.

Each of the measuring apparatuses 201 shown in FIG. 1 may be provided with a block for performing component analysis on the absorbing solution and detecting the existence of abnormal materials in the absorbing solution in addition to the blocks (211 to 214) for calculating dissolved $CO_2$ concentration in absorption solvent. Finding an abnormality in the absorbing solution on time by performing component analysis on the absorbing solution on time is thus enabled to further improve the stability of the operation of the system.

Such a block for abnormality detection (or the measuring apparatus 201 having such a block) may be provided in each of a plurality of places (upper, medium, and lower stages) in the absorption tower 101 and the regeneration tower 108 to enable monitoring on time whether or not any abnormality is occurring in the towers.

In the present embodiment, as described above, the dissolved $CO_2$ concentration is calculated from the ultrasound propagation speed in one or more measuring apparatuses 201 and system control is performed based on the calculated $CO_2$ concentrations. In the present embodiment, therefore, the dissolved $CO_2$ concentrations in the absorbing solutions can be grasped on time and the system can be stably and economically operated by means of system control based on the dissolved $CO_2$ concentrations.

In the present embodiment, four measuring apparatuses 201 are set in the vicinities of the inlets and outlets of the absorption tower 101 and the regeneration tower 108. However, the places in which measuring apparatuses 201 are set and the number of set measuring apparatuses 201 may be different from the described places and number.

In the present embodiment, the differences ΔX and ΔY are calculated from the dissolved $CO_2$ concentrations $X_1, X_2, Y_1$ and $Y_2$ and system control is performed based on the differences ΔX and ΔY. However, a different parameter may alternatively be calculated from the dissolved $CO_2$ concentrations $X_1, X_2, Y_1$ and $Y_2$ and system control may be performed based on this parameter.

(Examples of Method of Controlling System in FIG. 1)

Next, examples of the method of controlling the system in FIG. 1 are described.

In a first example, the system in FIG. 1 calculates an amount of recovered carbon dioxide in the system, based on the dissolved $CO_2$ concentration in the lean solution 104 supplied to the upper portion (top) of the absorption tower 101, and the dissolved $CO_2$ concentration in the rich solution 105 exhausted from the lower portion (bottom) of the absorption tower 101. Those concentrations are measured by the first and second measuring apparatuses 201.

In the first example, the system in FIG. 1 controls the flow rates of the lean solution 104 and the rich solution 105 so that the calculated amount of the recovered carbon dioxide becomes a predetermined amount. The calculated amount can be close to the predetermined amount by adjusting the balance between those flow rates.

In the first example, the system may control only one of the flow rates of the lean solution 104 and the rich solution 105, instead of controlling both of them. Alternately, the system may control the amount of heat inputted to the regeneration tower reboiler 109, or a rate of the flow rate of the lean solution 104 to the flow rate of the $CO_2$ containing gas 102 so that the calculated amount of the recovered carbon dioxide becomes the predetermined amount.

In the first example, the system may control at least two of the flow rate(s) of the lean solution 104 and/or the rich solution 105, the amount of heat inputted to the regeneration tower reboiler 109, and the rate of the flow rate of the lean solution 104 to the flow rate of the $CO_2$ containing gas 102. For example, the system may control the flow rate(s) of the lean solution 104 and/or the rich solution 105 so that the calculated amount of the recovered carbon dioxide becomes the predetermined amount, and then control the amount of heat inputted to the regeneration tower reboiler 109 into an amount corresponding to the flow rate(s).

In the first example, the system may control the flow rate of the lean solution 104, and/or the amount of heat inputted to the regeneration tower reboiler 109, based on the dissolved $CO_2$ concentration in the rich solution 105 exhausted from the lower portion of the absorption tower 101. The reason is that the dissolved $CO_2$ concentration in the rich solution 105 responds to a change of the carbon dioxide in the system faster than any other amounts. In this case, the system may include only the first measuring apparatus 201 among the first to fourth measuring apparatuses 201.

In a second example, the system in FIG. 1 calculates the amount of the recovered carbon dioxide in the system, based on the dissolved $CO_2$ concentration in the rich solution 105 supplied to the upper portion (top) of the regeneration tower 108, and the dissolved $CO_2$ concentration in the lean solution 104 exhausted from the lower portion (bottom) of the regeneration tower 108. Those concentrations are measured by the third and fourth measuring apparatuses 201. Usage of the calculated amount of the recovered carbon dioxide in the second example is as same as that in the first example.

In the second example, the system may control the flow rate of the lean solution 104, and/or the amount of heat inputted to the regeneration tower reboiler 109, based on the dissolved $CO_2$ concentration in the lean solution 104 exhausted from the lower portion of the regeneration tower 108. The reason is that the dissolved $CO_2$ concentration in the lean solution 104 can be used to determine whether it is required to increase the flow rate of the lean solution 104, or whether it is required to increase the amount of heat to reduce the dissolved $CO_2$ concentration in the lean solution 104, for example. In this case, the system may include only the fourth measuring apparatus 201 among the first to fourth measuring apparatuses 201.

In the present embodiment, the system can accurately measure the dissolved $CO_2$ concentrations of the lean solution 104 and the rich solution 105 even if those solutions 104 and 105 flow in the vicinity of the regeneration tower 108 placed near the heat source (regeneration tower reboiler 109), because those concentrations are measured by using the ultrasound. Therefore, according to the second example, the system can be accurately controlled similarly to the first example.

Second and third embodiments, which are examples of modifications of the first embodiment, will be described below mainly with respect to points of difference from the first embodiment.

Second Embodiment

Figure 3:
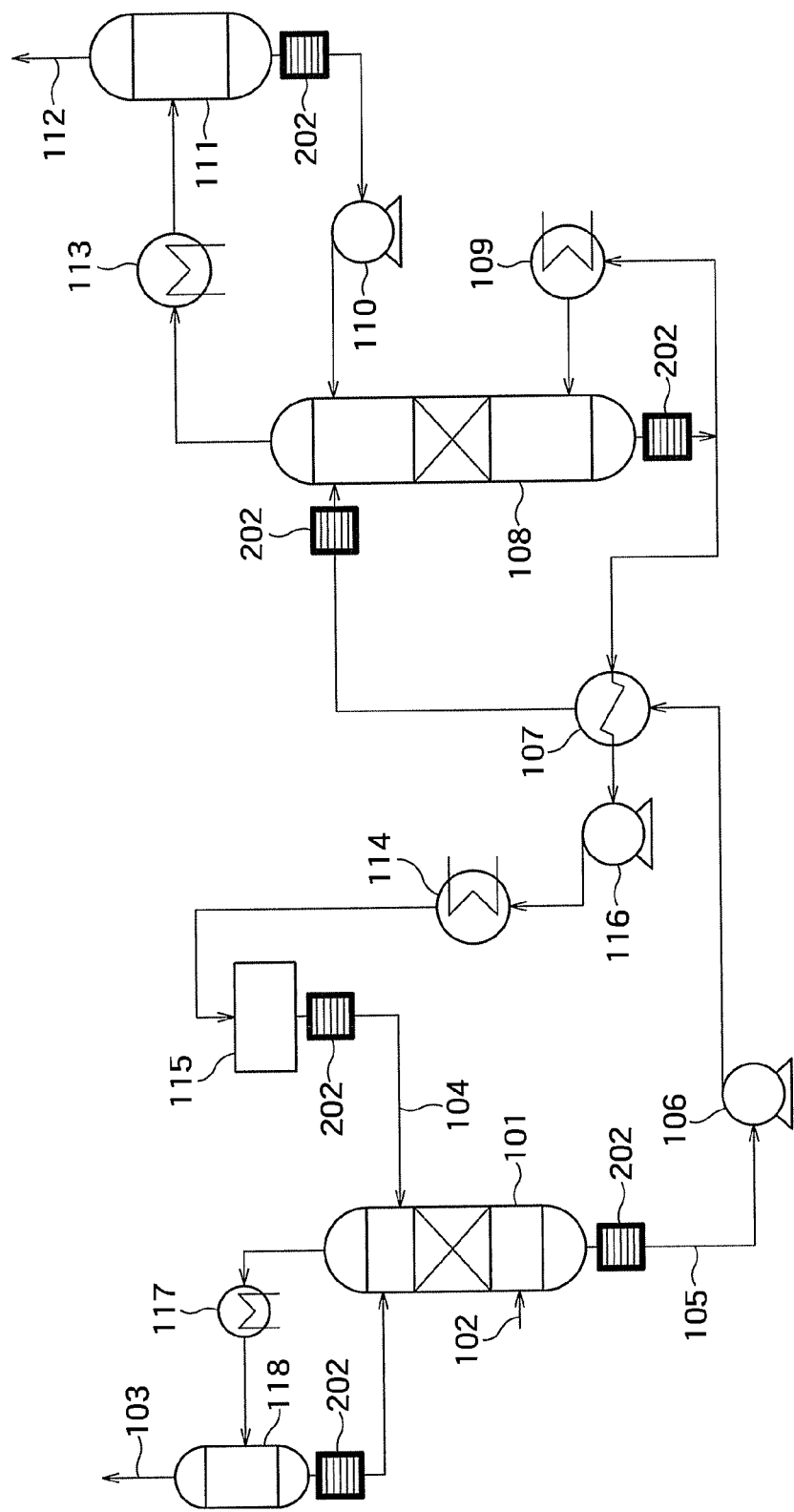
FIG. 3 is a diagram showing the construction of a carbon dioxide separating and recovering system in a second embodiment.

FIG. 3 is a diagram showing the construction of a carbon dioxide separating and recovering system in a second embodiment.

In the system shown in FIG. 1, in the first embodiment, one or more ultrasound propagation speed measuring apparatuses 201 that measure the ultrasound propagation speed in the absorbing solution flowing in the system are disposed. In the system shown in FIG. 3, in the second embodiment, one or more electric conductivity measuring apparatuses 202 that measure the electric conductivity of the absorbing solution (or condensed water) flowing in the system are disposed.

In the present embodiment, the measuring apparatuses 202 are disposed in the vicinities of the inlets and outlets of the absorption tower 101 and the regeneration tower 108, the condensed water outlet of the vapor-liquid disengager 118 and the condensed water outlet of the $CO_2$ separator 111. In FIG. 3, the six measuring apparatuses 202 disposed at such positions are shown.

In the present embodiment, with these measuring apparatuses 202, the electric conductivities of the lean solution 104 flowing in the vicinity of the inlet of the absorption tower 101, the rich solution 105 flowing in the vicinity of the outlet of the absorption tower 101, the rich solution 105 flowing in the vicinity of the inlet of the regeneration tower 108, the lean solution 104 flowing in the vicinity of the outlet of the regeneration tower 108, condensed water flowing in the vicinity of the outlet of the vapor-liquid disengager 118, and condensed water flowing in the vicinity of the outlet of the $CO_2$ separator 111 are measured. The measuring apparatuses 202 are an example of the first to sixth measuring apparatuses in the disclosure. In the present embodiment, each of the measuring apparatuses 202 is set in the channel in which the absorbing solution or condensed water flows (absorbing solution piping or condensed water piping).

Figure 4:
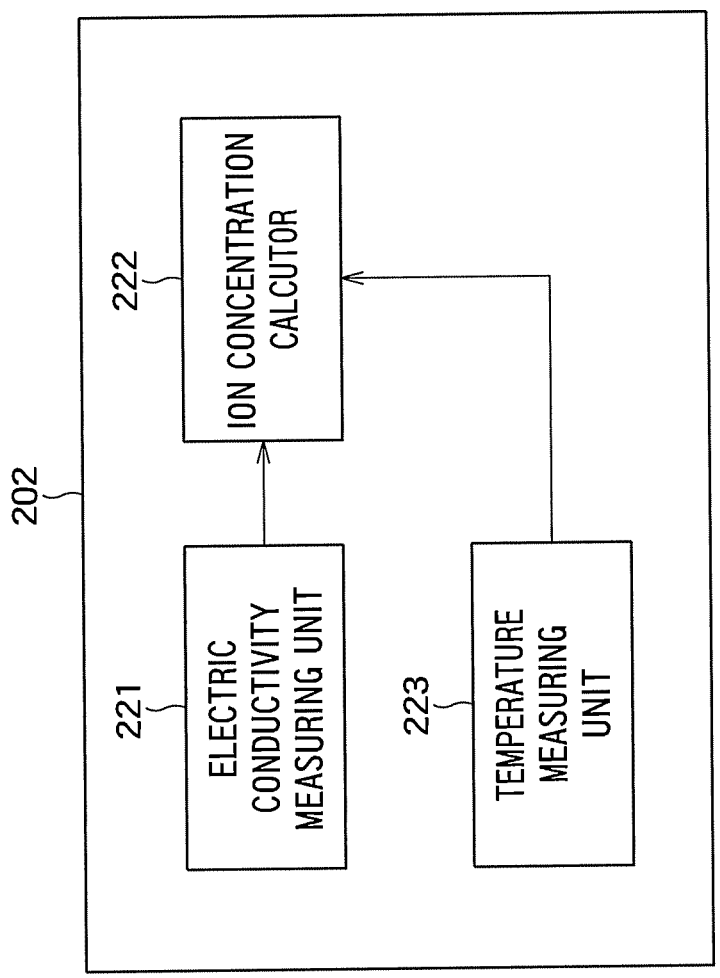
FIG. 4 is a block diagram showing a configuration of an electric conductivity measuring apparatus in FIG. 3.

FIG. 4 is a block diagram showing a configuration of the electric conductivity measuring apparatuses 202 in FIG. 3. Each of the electric conductivity measuring apparatuses 202 shown in FIG. 3 is assumed to have the configuration shown in FIG. 4.

The electric conductivity measuring apparatus 202 has, as shown in FIG. 4, an electric conductivity measuring unit 221, an ion concentration calculator 222 and a temperature measuring unit 223.

The electric conductivity measuring unit 221 is a device that measures the electric conductivity of the absorbing solution or condensed water. The temperature measuring unit 223 is a thermometer that measures the temperature of the absorbing solution or condensed water. The electric conductivity measuring unit 221 and the temperature measuring unit 223 are disposed close to each other so that a place in which the electric conductivity is measured and a place in which the temperature is measured are close to each other.

Figure 10:
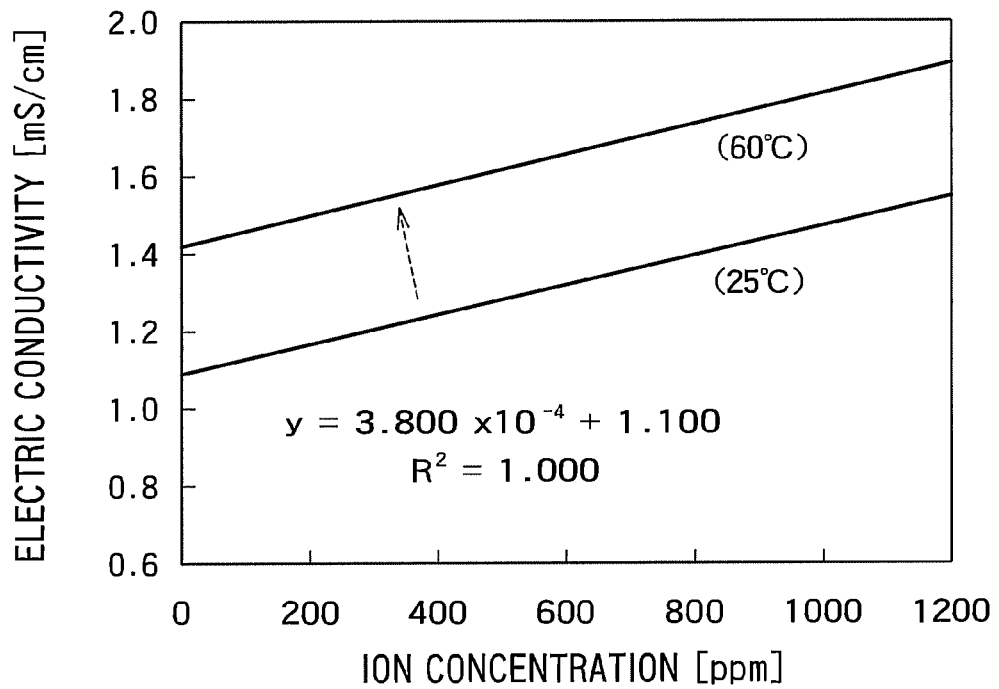
FIG. 10 is a graph showing the relationship between the ion concentration and the electric conductivity.

The electric conductivity of the absorbing solution or condensed water is a parameter usable for calculation of the ion concentration in the absorbing solution or condensed water, as described below with reference to FIG. 10. FIG. 10 is a graph showing the relationship between the ion concentration and the electric conductivity in the absorbing solution. As shown in FIG. 10, the electric conductivity in the absorbing solution changes according to the ion concentration in the absorbing solution. Therefore the ion concentration in the absorbing solution can be calculated from the electric conductivity of the absorbing solution. The same can also be said with respect to water. The ion concentration in condensed water can be calculated from the electric conductivity of condensed water.

However, the electric conductivity of the absorbing solution or condensed water also changes depending on the temperature of the absorbing solution or condensed water, as does the ultrasound propagation speed. That is, the electric conductivity has a temperature dependence. Therefore, a correlation expression shown in FIG. 10 is changed according to the temperature of the absorbing solution. FIG. 10 shows the correlation expression at 25° C. and at 60° C., i.e., a state in which the correlation expression is changed according to the temperature.

To be more specific, the electric conductivity of the absorbing solution or condensed water changes according to the total ion concentration in the absorbing solution or condensed water. Accordingly, a large or small amount of impurity product ions contained in the absorbing solution or condensed water also contributes to a high or low electric conductivity. Conversely, the degree of electric conductivity can be used for evaluation of the amount of impurity product ions contained in the absorbing solution or condensed water. Details of a method for this evaluation will be described below. The abscissa of the graph shown in FIG. 10 represents the total ion concentration in the absorbing solution.

As described above, the ion concentration in the absorbing solution or condensed water can be calculated from the electric conductivity of the absorbing solution or condensed water. In the present embodiment, therefore, a correlation expression showing the relationship between the electric conductivity and the ion concentration in the absorbing solution or condensed water is obtained in advance and saved in the measuring apparatus 202. In the present embodiment, a straight line expressed by the correlation expression, such as shown in FIG. 10, is used as a measuring line for measuring the ion concentration. In this way, the measuring apparatus 202 can calculate the ion concentration from the electric conductivity.

However, the above-described correlation expression has a temperature dependence. In the present embodiment, therefore, the above-described correlation expressions at various temperatures are saved in the measuring apparatus 202. Alternatively, a fixed expression including temperature as a parameter is formed from the above-described correlation expression and saved in the measuring apparatus 202, thus enabling calculation of the ion concentration taking temperature compensation into consideration.

The measuring apparatus 202 in the present embodiment calculates the ion concentration in the absorbing solution or condensed water based on the temperature of the absorbing solution or condensed water, the electric conductivity in the absorbing solution or condensed water and the above-described correlation expression. The ion concentration calculator 222 (see FIG. 4), which is a block relating to this processing, will be described below in detail.

The ion concentration calculator 222 is a block for calculating the ion concentration in the absorbing solution or condensed water on the basis of the temperature measured by the temperature measuring unit 223, the electric conductivity measured by the electric conductivity measuring unit 221, and the above-described correlation expression. For example, the ion concentration calculator 222 is constituted by a storage unit capable of storing the above-described correlation expression and a calculator that performs processing for calculating the ion concentration.

In the present embodiment, as described above, a method of calculating the ion concentration in the absorbing solution or condensed water from the electric conductivity in the absorbing solution or condensed water is adopted. As in the case of calculating the dissolved $CO_2$ concentration from the ultrasound propagation speed, this method has the advantage of enabling on-time grasping of the ion concentration.

From the electric conductivity of the absorbing solution or condensed water, the total ion concentration in the absorbing solution or condensed water is calculated, as described above. On the other hand, in the system in the present embodiment, ions probable to exist in the absorbing solution or condensed water are impurity product ions. In the present embodiment, therefore, when impurity product ions are produced in the absorbing solution or condensed water, the total ion concentration in the absorbing solution or condensed water is increased to cause increase in electric conductivity. In the present embodiment, therefore, the ion concentration of impurity product ions contained in the absorbing solution or condensed water can be calculated from the electric conductivity of the absorbing solution or condensed water.

It is known that impurity product ions in the absorbing solution cause degradation in the $CO_2$ absorbing performance of the absorbing solution and influence mass and heat balances in the system. Also, since condensed water is returned to the absorbing solution in the absorption tower 101 and the regeneration tower 108, impurity product ions in condensed water also influence mass and heat balances in the system.

In the present embodiment, the ion concentrations in the absorbing solution and condensed water are monitored on time and the mass and heat balances in the system are controlled based on the monitored ion concentrations. For example, the amount of heat inputted to the regeneration tower reboiler 109 and the flow rate of the $CO_2$ containing gas 102 supplied to the absorption tower 101 are adjusted. In the present embodiment, the system can be stably and economically operated in this way.

System control in the present embodiment performed based on the ion concentration calculated by the measuring apparatus 202 will be described below in detail.

In the system shown in FIG. 3, the ion concentrations in the absorbing solutions flowing in the vicinities of the inlets and outlets of the absorption tower 101 and the regeneration tower 108 and the ion concentrations in condensed water flowing in the vicinities of the outlets of the vapor-liquid disengager 118 and the $CO_2$ separator 111 are calculated by the six measuring apparatuses 202, as described above. The ion concentrations in the vicinities of the inlet of the absorption tower 101, the outlet of the absorption tower 101, the inlet of the regeneration tower 108, the outlet of the regeneration tower 108, the outlet of the vapor-liquid disengager 118 and the outlet of the $CO_2$ separator 111 are represented by $\Delta_1$, $\Delta_2$, $\beta_1$, $\beta_2$, $\gamma_1$, and $\gamma_2$, respectively.

In the system shown in FIG. 3, control of the system is performed based on these ion concentrations $\alpha_1$, $\alpha_2$, $\beta_1$, $\beta_2$, $\gamma_1$, and $\gamma_2$, as described below.

For example, when the ion concentrations $\alpha_1$, $\alpha_2$, and $\gamma_1$ in the vicinities of the absorption tower 101 exceed a predetermined upper limit value, a state where the $CO_2$ absorbing performance of the absorbing solution flowing in the vicinity of the absorption tower 101 is reduced is recognized. Then, in the system shown in FIG. 3, the operation of the regeneration tower reboiler 109 is controlled so that the thermal energy input to the regeneration tower reboiler 109 is reduced, thereby reducing the amount of $CO_2$ released at the regeneration tower 108.

Conversely, when the ion concentrations $\beta_1$, $\beta_2$, and $\gamma_2$ in the vicinities of the regeneration tower 108 exceed a predetermined upper limit value, a state where the $CO_2$ absorbing performance of the absorbing solution flowing in the vicinity of the regeneration tower 108 is reduced is recognized. Then, in the system shown in FIG. 3, the operation of the regeneration tower reboiler 109 is controlled so that the thermal energy input to the regeneration tower reboiler 109 is increased, thereby reducing the amount of $CO_2$ released at the regeneration tower 108.

In the above-described system control in the present embodiment, control of the flow rate of the $CO_2$ containing gas 102 supplied to the absorption tower 101, the circulation flow rate of the rich solution 105 flowed from the absorption tower 101 to the regeneration tower 108, the flow rate of the lean solution 104 flowing between the regeneration tower 108, the regeneration tower reboiler 109 and the absorption tower 101 or a condition for agitation in the lean solution buffer tank 115 may be performed instead of control of the amount of heat inputted to the regeneration tower reboiler 109. Two or more of these operating conditions may alternatively be controlled. Through control of these operating conditions, stable economical operation of the system can also be realized.

In the present embodiment, when certain ones of the ion concentrations $\alpha_1$, $\alpha_2$, $\beta_1$, $\beta_2$, $\gamma_1$ and $\gamma_2$ exceed the predetermined upper limit, processing for removing impurity product ions from the absorbing solution and condensed water and processing for changing the pure absorbing solution may be further performed. Removal of impurity product ions can be executed, for example, by using an ion-exchange resin.

In the present embodiment, as described above, the ion concentration is calculated from the electric conductivity in one or more measuring apparatuses 202. System control is performed based on the calculated ion concentrations. In the present embodiment, therefore, the ion concentrations in the absorbing solutions and condensed water can be grasped on time and the system can be stably and economically operated by means of system control based on the ion concentrations.

In the present embodiment, six measuring apparatuses 202 are set in the vicinities of the inlets and outlets of the absorption tower 101 and the regeneration tower 108 and the outlets of the vapor-liquid disengager 118 and the $CO_2$ separator 111. However, the places in which measuring apparatuses 202 are set and the number of set measuring apparatuses 202 may be different from the described places and number. For example, only four measuring apparatuses 202 may be set in the vicinities of the inlets and outlets of the absorption tower 101 and the regeneration tower 108.

Third Embodiment

Figure 5:
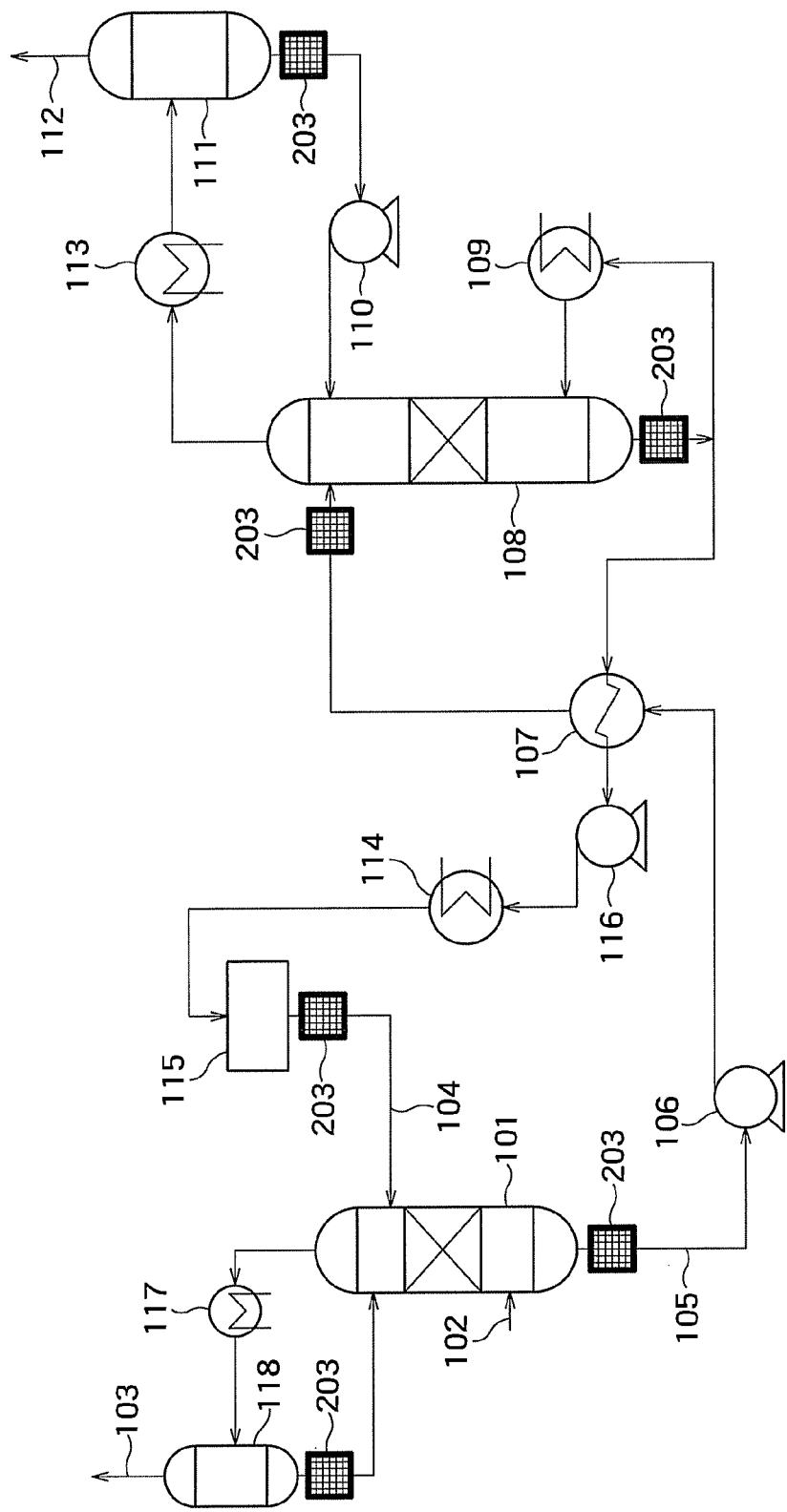
FIG. 5 is a diagram showing the construction of a carbon dioxide separating and recovering system in a third embodiment.

FIG. 5 is a diagram showing the construction of a carbon dioxide separating and recovering system in a third embodiment.

In the system shown in FIG. 5, in the present embodiment, one or more ultrasound propagation speed/electric conductivity measuring apparatuses 203 that measure the ultrasound propagation speed and electric conductivity in the absorbing solution (or condensed water) flowing in the system are disposed.

In the present embodiment, these measuring apparatuses 203 are disposed in the vicinities of the inlets and outlets of the absorption tower 101 and the regeneration tower 108, the condensed water outlet of the vapor-liquid disengager 118 and the condensed water outlet of the $CO_2$ separator 111. In FIG. 5, the six measuring apparatuses 203 disposed at such positions are shown.

In the present embodiment, with these measuring apparatuses 203, the ultrasound propagation speeds and the electric conductivities of the lean solution 104 flowing in the vicinity of the inlet of the absorption tower 101, the rich solution 105 flowing in the vicinity of the outlet of the absorption tower 101, the rich solution 105 flowing in the vicinity of the inlet of the regeneration tower 108, the lean solution 104 flowing in the vicinity of the outlet of the regeneration tower 108, condensed water flowing in the vicinity of the outlet of the vapor-liquid disengager 118, and condensed water flowing in the vicinity of the outlet of the $CO_2$ separator 111 are measured. The measuring apparatuses 203 are an example of the first to sixth measuring apparatuses in the disclosure. In the present embodiment, each of the measuring apparatuses 203 is set in the channel in which the absorbing solution or condensed water flows (absorbing solution piping or condensed water piping).

Figure 6:
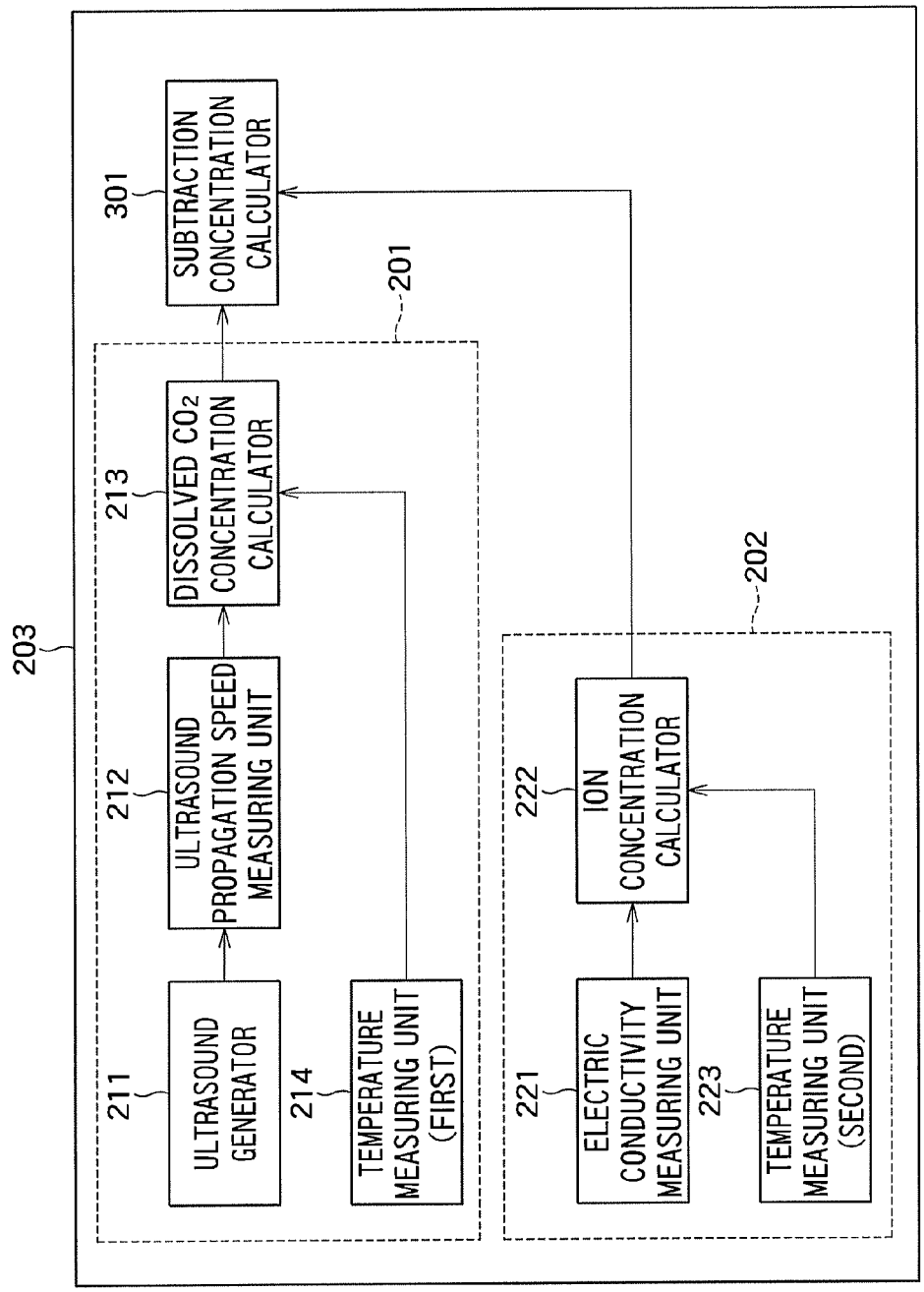
FIG. 6 is a block diagram showing a first exemplary configuration of an ultrasound propagation speed and electric conductivity measuring apparatus in FIG. 5.
Figure 7:
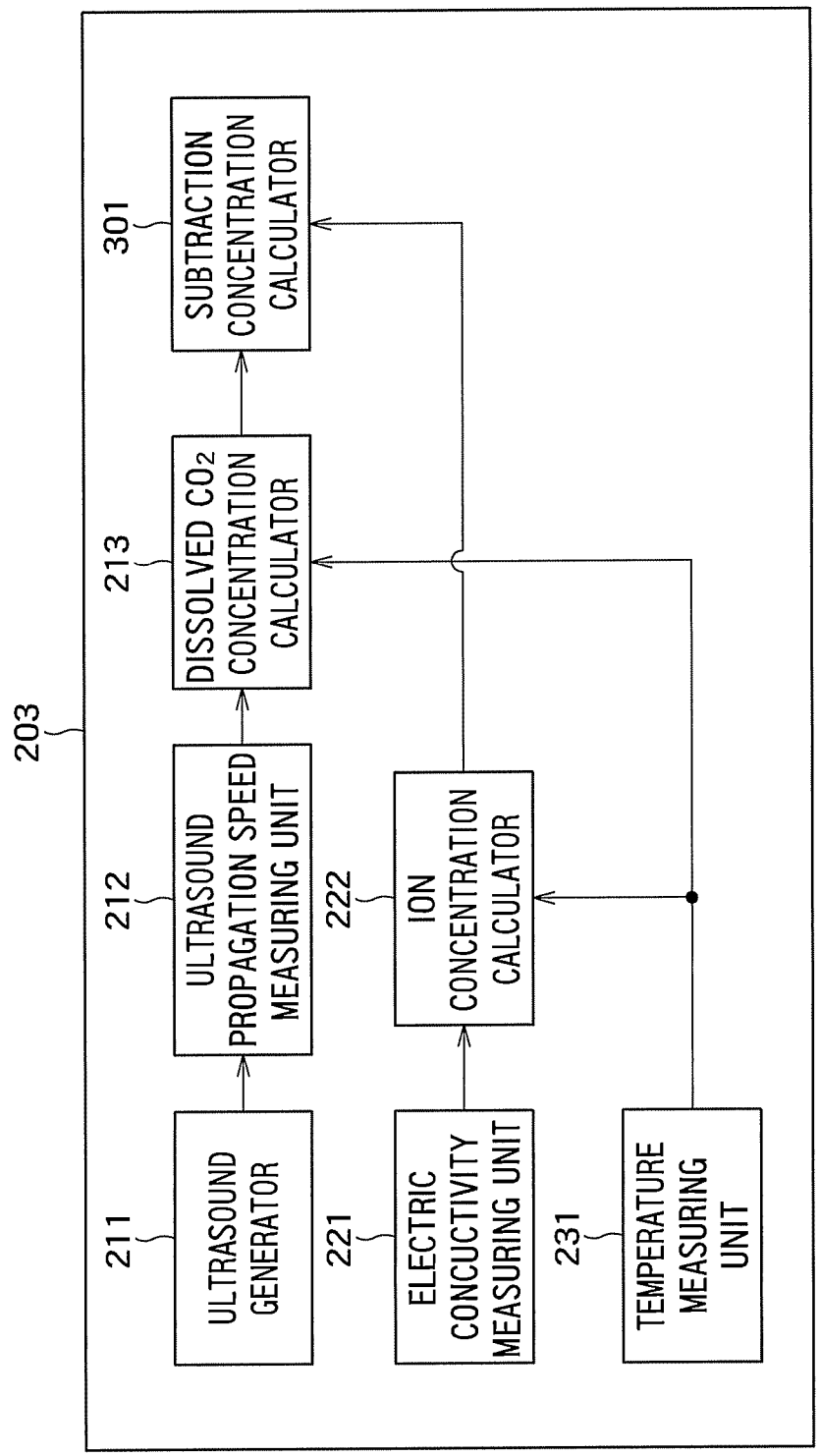
FIG. 7 is a block diagram showing a second exemplary configuration of the ultrasound propagation speed and electric conductivity measuring apparatus in FIG. 5.

FIGS. 6 and 7 are block diagrams showing first and second exemplary configurations of the ultrasound propagation speed and electric conductivity measuring apparatuses 203 in FIG. 5. Each of the electric conductivity measuring apparatuses 203 shown in FIG. 5 is assumed to have the configuration shown in FIG. 6 or 7.

The measuring apparatus 203 shown in FIG. 6 is configured like a combination of the measuring apparatus 201 shown in FIG. 2 and the measuring apparatus 202 shown in FIG. 4, and has an ultrasound generator 211, an ultrasound propagation speed measuring unit 212, a dissolved $CO_2$ concentration calculator 213, a temperature measuring unit 214, an electric conductivity measuring unit 221, an ion concentration calculator 222, and a temperature measuring unit 223. The configurations of these blocks are the same as those shown in FIGS. 2 and 4.

On the other hand, the measuring apparatus 203 shown in FIG. 7 is configured in such a manner that the temperature measuring units 214 and 223 in FIG. 6 are replaced with a temperature measuring unit 231. This is a result of removal of the wasteful coexistence of the two temperature measuring units 214 and 223 in one measuring apparatus 203. The temperature measured by the temperature measuring unit 231 is used for calculation of the dissolved $CO_2$ concentration performed by the dissolved $CO_2$ concentration calculator 213 and for calculation of the ion concentration performed by the ion concentration calculator 222.

It should be noted that the temperature measuring units 214 and 223 in FIG. 6 are examples of the first and second temperature measuring units of the disclosure respectively.

According to the present embodiment, system control in a mode based on a combination of the first and second embodiments can be performed. For example, according to the present embodiment, the system can be stably and economically operated by monitoring the dissolved $CO_2$ concentration and the ion concentration in the absorbing solution on time and by performing mass and heat balance control on the system based on the dissolved $CO_2$ concentration and the ion concentration. Because both the dissolved $CO_2$ concentration and the ion concentration are considered in such mass and heat balance control, system control more suitable than those in the first and second embodiments is enabled.

In the present embodiment, system control may be performed based on a subtraction concentration calculated by a subtraction concentration calculator 301 shown in FIG. 6 or 7. The subtraction concentration is a dissolved $CO_2$ concentration obtained by subtracting the ion concentration calculated by the ion concentration calculator 222 from the dissolved $CO_2$ concentration calculated by the dissolved $CO_2$ concentration calculator 213.

The dissolved $CO_2$ concentration calculator 213 calculates the dissolved $CO_2$ concentration from the ultrasound propagation speed. The dissolved $CO_2$ concentration calculated in this way includes the effect of impurity product ions in addition to the dissolved $CO_2$ concentration itself. Therefore, the dissolved $CO_2$ concentration calculated is not a correct value unless the effect of impurity product ions is subtracted therefrom.

Therefore, the subtraction concentration calculator 301 in the present embodiment calculates the dissolved $CO_2$ concentration (subtraction concentration) by subtracting the ion concentration (ion concentration of impurity product ions) calculated by the ion concentration calculator 222 from the dissolved $CO_2$ concentration calculated by the dissolved $CO_2$ concentration calculator 213. However, if there is a need to convert the ion concentration into a dissolved $CO_2$ concentration at the time of subtraction of the ion concentration from the dissolved $CO_2$ concentration, subtraction is performed after making the necessary conversion.

In the present embodiment, system control is performed based on the calculated subtraction concentration. According to the present embodiment, the system can be stably and economically operated by monitoring the subtraction concentration in the absorbing solution on time and by performing mass and heat balance control on the system based on the subtraction concentration. Because the accurate dissolved $CO_2$ concentration can be used in this mass and heat balance control, system control more suitable than that in the first embodiment is enabled.

When system control based on the subtraction concentration is performed, system control may be performed based on the difference calculated between the subtraction concentrations in the vicinities of the inlet and the outlet of the absorption tower 101 and the difference calculated between the subtraction concentrations in the vicinities of the inlet and the outlet of the regeneration tower 108, as is that in the first embodiment.

In the present embodiment, as described above, the dissolved $CO_2$ concentration and the ion concentration are calculated from the ultrasound propagation speed and the electric conductivity in one or more measuring apparatuses 203, and system control is performed based the dissolved $CO_2$ concentration and the ion concentration. In the present embodiment, therefore, the dissolved $CO_2$ concentrations and the ion concentrations in the absorbing solution and condensed water can be grasped on time and the system can be stably and economically operated by means of system control based on the dissolved $CO_2$ concentrations and the ion concentrations.

In the present embodiment, six measuring apparatuses 203 are set in the vicinities of the inlets and outlets of the absorption tower 101 and the regeneration tower 108 and the outlets of the vapor-liquid disengager 118 and the $CO_2$ separator 111. However, the places in which measuring apparatuses 203 are set and the number of set measuring apparatuses 203 may be different from the described places and number. For example, only four measuring apparatuses 203 may be set in the vicinities of the inlets and outlets of the absorption tower 101 and the regeneration tower 108.

In a case where the ion concentration of the impurity product ions in the absorbing solution is low, the electric conductivity measured by the electric conductivity measuring unit 221 can be used to calculate a $CO_2$ ion concentration in the absorbing solution, because effects of the impurity product ions on the electric conductivity is small. Therefore, in such case, the ion concentration calculator 222 can calculate the $CO_2$ ion concentration in the absorbing solution, based on the electric conductivity measured by the electric conductivity measuring unit 221.

Therefore, the system of the present embodiment may be controlled based on the dissolved $CO_2$ concentration measured by the dissolved $CO_2$ concentration calculator 213, and the $CO_2$ ion concentration measured by the ion concentration calculator 222.

Examples of usage of those concentrations include 1) calculating a mean value of the concentrations, 2) determining anomalous occurrence if the difference between the concentrations are large, and 3) using a preferred concentration depending on the situation. For example, in a case where the ion concentration of the impurity product ions in the absorbing solution is high, the $CO_2$ ion concentration measured by the ion concentration calculator 222 is not accurate. Therefore, in such case, it is preferred to use the dissolved $CO_2$ concentration measured by the dissolved $CO_2$ concentration calculator 213.

The ion concentration calculator 222 calculating the $CO_2$ ion concentration in the absorbing solution can also be applied to the second embodiment.

(Place to Dispose Measuring Apparatus)

Description will be finally made of places where the individual measuring apparatuses 201 to 203 are disposed.

Figure 11:
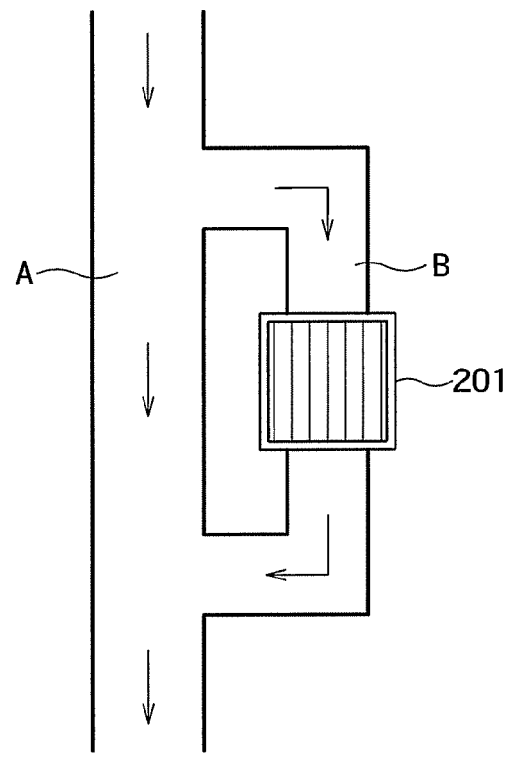
FIG. 11 is a diagram showing a place where the ultrasound propagation speed measuring apparatus is disposed.

FIG. 11 is a diagram showing a place where an ultrasound propagation speed measuring apparatuses 201 is disposed.

FIG. 11 shows, as channels through which the absorbing solution flows (absorbing solution piping), a channel A corresponding to the main flow and a bypass channel B provided as a bypass bypassing the channel A. Examples of the channel A are the channel for the rich solution 105 connecting the outlet of the absorption tower 101 and the inlet of the regeneration tower 108 and the channel for the lean solution 104 connecting the outlet of the regeneration tower 108 and the inlet of the absorption tower 101.

It is desirable to dispose the measuring apparatus 201 in a place where the amount of air bubbles in the absorbing solution is smaller in order to accurately measure the ultrasound propagation speed. In general, while the amount of air bubbles in the absorbing solution is large in the channel A corresponding to a main flow, the amount of air bubbles in the absorbing solution in the bypass channel B bypassing the main-flow channel A is smaller than that in the main-flow channel A. In the present embodiment, therefore, each measuring apparatus 201 is disposed in the bypass channel B to measure the ultrasound propagation speed in the absorbing solution flowing in the bypass channel B.

Similarly, in the second and third embodiments, each of the measuring apparatuses 202 and 203 is disposed in a bypass channel bypassing the channel for the absorbing solution or condensed water to measure the ultrasound propagation speed and the electric conductivity in the absorbing solution or condensed water flowing through the bypass channel.

In measuring the ultrasound propagation speed and the electric conductivity in the vicinity of the inlet or the outlet of the absorption tower 101, it is desirable that the temperature of the absorbing solution be 30 to 50° C. In measuring the ultrasound propagation speed and the electric conductivity in the vicinity of the inlet or the outlet of the regeneration tower 108, it is desirable that the temperature of the absorbing solution be 100 to 130° C.

While certain embodiments have been described, these embodiments have been presented by way of example only, and are not intended to limit the scope of the inventions. Indeed, the novel systems and methods described herein may be embodied in a variety of other forms; furthermore, various omissions, substitutions and changes in the form of the systems and methods described herein may be made without departing from the spirit of the inventions. The accompanying claims and their equivalents are intended to cover such forms or modifications as would fall within the scope and spirit of the inventions.

The invention claimed is:

1. A carbon dioxide separating and recovering system comprising:
   an absorption tower configured to cause carbon dioxide to be absorbed in an absorbing solution, and exhaust a rich solution as the absorbing solution in which the carbon dioxide is absorbed;
   a regeneration tower configured to release the carbon dioxide from the rich solution, and exhaust a lean solution as the absorbing solution having a dissolved carbon dioxide concentration lower than a dissolved carbon dioxide concentration in the rich solution;
   a rich solution transferring pump configured to transfer the rich solution from an outlet of the absorption tower to an inlet of the regeneration tower;
   a lean solution transferring pump configured to transfer the lean solution from an outlet of the regeneration tower to an inlet of the absorption tower; and
   at least one measuring apparatus configured to measure an ultrasound propagation speed in the absorbing solution flowing in the system, each of the at least one measuring apparatus comprising:
      a temperature measuring unit configured to measure a temperature of the absorbing solution;
      an ultrasound generator configured to generate ultrasound in the absorbing solution;
      an ultrasound propagation speed measuring unit configured to measure the ultrasound propagation speed by using the ultrasound; and
      a dissolved carbon dioxide concentration calculator configured to calculate a dissolved carbon dioxide concentration in the absorbing solution, based on the temperature measured by the temperature measuring unit, the ultrasound propagation speed measured by the ultrasound propagation speed measuring unit, and a correlation expression which shows a relationship between the dissolved carbon dioxide concentration and the ultrasound propagation speed in the absorbing solution, and is changed according to the temperature of the absorbing solution,
   wherein the at least one measuring apparatus comprises first to fourth measuring apparatuses configured to measure the ultrasound propagation speeds in the lean solution flowing in a vicinity of the inlet of the absorption tower, in the rich solution flowing in a vicinity of the outlet of the absorption tower, in the rich solution flowing in a vicinity of the inlet of the regeneration tower, and in the lean solution flowing in a vicinity of the outlet of the regeneration tower, respectively, and wherein the carbon dioxide separating and recovering system is configured to control the system, based on the dissolved carbon dioxide concentrations calculated by the measuring apparatuses.

2. A carbon dioxide separating and recovering system comprising:

an absorption tower configured to cause carbon dioxide to be absorbed in an absorbing solution, and exhaust a rich solution as the absorbing solution in which the carbon dioxide is absorbed;

a regeneration tower configured to release the carbon dioxide from the rich solution, and exhaust a lean solution as the absorbing solution having a dissolved carbon dioxide concentration lower than a dissolved carbon dioxide concentration in the rich solution; and at least one measuring apparatus configured to measure an ultrasound propagation speed in the absorbing solution flowing in the system, each of the at least one measuring apparatus comprising:

a temperature measuring unit configured to measure a temperature of the absorbing solution;

an ultrasound generator configured to generate ultrasound in the absorbing solution;

an ultrasound propagation speed measuring unit configured to measure the ultrasound propagation speed by using the ultrasound;

a dissolved carbon dioxide concentration calculator configured to calculate a dissolved carbon dioxide concentration in the absorbing solution, based on the temperature measured by the temperature measuring unit, the ultrasound propagation speed measured by the ultrasound propagation speed measuring unit, and a correlation expression which shows a relationship between the dissolved carbon dioxide concentration and the ultrasound propagation speed in the absorbing solution, and is changed according to the temperature of the absorbing solution;

an electric conductivity measuring unit configured to measure electric conductivity of the absorbing solution; and an ion concentration calculator configured to calculate an ion concentration in the absorbing solution, based on the temperature measured by the temperature measuring unit or a second temperature measuring unit in the measuring apparatus, the electric conductivity measured by the electric conductivity measuring unit, and a correlation expression which shows a relationship between the ion concentration and the electric conductivity in the absorbing solution, and is changed according to the temperature of the absorbing solution, wherein the carbon dioxide separating and recovering system is configured to control the system, based on the dissolved carbon dioxide concentration and the ion concentration calculated by the measuring apparatus.

3. The system of claim 2, wherein each of the at least one measuring apparatus further comprises:

a subtraction concentration calculator configured to calculate a subtraction concentration by subtracting the ion concentration of impurity product ions calculated by the ion concentration calculator from the dissolved carbon dioxide concentration calculated by the dissolved carbon dioxide concentration calculator, wherein the carbon dioxide separating and recovering system controls the system, based on the subtraction concentration calculated by the measuring apparatus.

4. The system of claim 2, wherein the ion concentration calculator is configured to calculate the ion concentration of carbon dioxide ions in the absorbing solution, and the carbon dioxide separating and recovering system is configured to control the system, based on the dissolved carbon dioxide concentration and the ion concentration of the carbon dioxide ions.

5. A method of controlling a carbon dioxide separating and recovering system, the system comprising (i) an absorption tower configured to cause carbon dioxide to be absorbed in an absorbing solution, and exhaust a rich solution as the absorbing solution in which the carbon dioxide is absorbed, and (ii) a regeneration tower configured to release the carbon dioxide from the rich solution, and exhaust a lean solution as the absorbing solution having a dissolved carbon dioxide concentration lower than a dissolved carbon dioxide concentration in the rich solution, wherein the method comprises:

measuring a temperature of the absorbing solution flowing in the system;

generating ultrasound in the absorbing solution;

measuring an ultrasound propagation speed in the absorbing solution by using the ultrasound;

calculating a dissolved carbon dioxide concentration in the absorbing solution, based on the measured temperature, the measured ultrasound propagation speed, and a correlation expression which shows a relationship between the dissolved carbon dioxide concentration and the ultrasound propagation speed in the absorbing solution, and is changed according to the temperature of the absorbing solution; and controlling the system, based on the calculated dissolved carbon dioxide concentration.

* * * * *